US006937885B1

(12) United States Patent
Lewis et al.

(10) Patent No.: US 6,937,885 B1
(45) Date of Patent: Aug. 30, 2005

(54) MULTISPECTRAL/HYPERSPECTRAL MEDICAL INSTRUMENT

(75) Inventors: Edgar N. Lewis, Brookeville, MD (US); Jenny E. Freeman, Chestnut Hill, MA (US)

(73) Assignee: HyperMed, Inc., Weston, MA (US)

( * ) Notice: Subject to any disclaimer, the term of this patent is extended or adjusted under 35 U.S.C. 154(b) by 0 days.

(21) Appl. No.: 09/182,898

(22) Filed: Oct. 30, 1998

Related U.S. Application Data (60) Provisional application No. 60/093,041, filed on Nov. 10, 1997.

(51) Int. Cl.[7] .............................................. A61B 6/00
(52) U.S. Cl. ...................................... 600/476; 128/920
(58) Field of Search ............................... 600/473, 475, 600/476, 477, 478, 479; 356/301, 302, 303, 356/307, 308, 311, 317, 318, 319, 320; 250/461.2; 128/920

(56) References Cited

U.S. PATENT DOCUMENTS

| | | | |
|---|---|---|---|
| 4,817,623 A | 4/1989 | Stoddart et al. ............. 128/665 |
| 4,902,136 A | 2/1990 | Mueller et al. .............. 356/419 |
| 5,079,698 A | 1/1992 | Grenier et al. ......... 364/413.13 |
| 5,104,392 A | 4/1992 | Kittrell et al. ................. 606/15 |
| 5,125,404 A | 6/1992 | Kittrell et al. ............... 128/634 |
| 5,140,989 A | 8/1992 | Lewis et al. ................ 128/665 |
| 5,174,297 A * | 12/1992 | Daikuzono ................... 128/665 |
| 5,213,105 A | 5/1993 | Gratton et al. .............. 128/664 |
| 5,216,484 A | 6/1993 | Chao et al. .................. 356/326 |
| 5,217,013 A | 6/1993 | Lewis et al. ................ 128/633 |
| 5,307,813 A | 5/1994 | Young ...................... 128/653.4 |
| 5,318,023 A | 6/1994 | Vari et al. .................... 128/633 |
| 5,318,024 A | 6/1994 | Kittrell et al. ............... 128/634 |
| 5,341,805 A | 8/1994 | Stavridi et al. .............. 128/633 |
| 5,349,961 A | 9/1994 | Stoddart et al. ............. 128/665 |
| 5,353,790 A | 10/1994 | Jacques et al. .............. 128/633 |
| 5,377,003 A | 12/1994 | Lewis et al. ................. 356/300 |
| 5,377,676 A | 1/1995 | Vari et al. .................... 128/634 |
| 5,421,337 A | 6/1995 | Richards-Kortum et al. ..... 128/665 |
| 5,452,723 A | 9/1995 | Wu et al. ..................... 128/664 |
| 5,456,252 A | 10/1995 | Vari et al. .................... 128/633 |
| 5,461,477 A | 10/1995 | Marinelli et al. ............ 356/352 |
| 5,507,287 A | 4/1996 | Palcic et al. ................. 128/633 |
| 5,528,368 A | 6/1996 | Lewis et al. ................. 356/346 |
| 5,539,517 A | 7/1996 | Cabib et al. ................. 356/346 |

(Continued)

FOREIGN PATENT DOCUMENTS

WO    PCT/CA98/00292    4/1998

(Continued)

OTHER PUBLICATIONS

Lewis, et al., "Fourier Transform Spectroscopic Imaging Using an Infrared Focal-Plane Array Detector,"*Analytical Chemistry*, vol. 67, No. 19, Oct. 1, 1995, pp. 3377-3381.

(Continued)

*Primary Examiner*—Eleni Mantis Mercader
(74) *Attorney, Agent, or Firm*—Powell Goldstein LLP (57) ABSTRACT

A medical instrument that comprises: a first-stage optic responsive to a tissue surface of a patient; a spectral separator optically responsive to the first stage optic and having a control input; an imaging sensor optically responsive to the spectral separator and having an image data output; and a diagnostic processor having an image acquisition interface with an input responsive to the imaging sensor and a filter control interface having a control output provided to the control input of the spectral separator.

87 Claims, 3 Drawing Sheets

U.S. PATENT DOCUMENTS

| | | | |
|---|---|---|---|
| 5,553,614 A | 9/1996 | Chance | 128/633 |
| 5,587,585 A | 12/1996 | Eisen et al. | 250/370.09 |
| 5,590,660 A | 1/1997 | MacAulay et al. | 128/664 |
| 5,591,981 A | 1/1997 | Heffelfinger et al. | 250/458.1 |
| 5,606,413 A | 2/1997 | Bellus et al. | 356/326 |
| 5,647,368 A | 7/1997 | Zeng et al. | 128/665 |
| 5,678,550 A | 10/1997 | Bassen et al. | 128/654 |
| 5,697,373 A * | 12/1997 | Richards-Kortum | 128/664 |
| 5,733,739 A * | 3/1998 | Zakim et al. | 435/29 |
| 5,813,987 A * | 9/1998 | Modell et al. | 600/473 |
| 5,864,397 A * | 1/1999 | Vo-Dinh | 356/301 |
| 5,938,617 A * | 8/1999 | Vo-Dinh | 600/476 |
| 5,991,653 A * | 11/1999 | Richards-Kortum | 600/475 |
| 6,008,492 A * | 12/1999 | Slater et al. | 250/334 |
| 6,640,132 B1 * | 10/2003 | Freeman et al. | 600/476 |

FOREIGN PATENT DOCUMENTS

| | | |
|---|---|---|
| WO | PCT/US98/14564 | 7/1998 |

OTHER PUBLICATIONS

Lewis, et al., "Real-Time, Mid-Infrared Spectroscopic Imaging Microscopy Using Indium Antimonide Focal-Plane Array Detection,"*Applied Spectroscopy*, vol. 49, No. 5, 1995, pp. 672-678.

Goldstein, et al., "The design and implementation of a high-fidelity Raman imaging microscope,"*Journal of Microscopy*, vol. 184, Oct. 1996, pp. 35-45.

Lewis, et al., "High-Fidelity Fourier Transform Infrared Spectroscopic Imaging of Primate Brain Tissue,"*Applied Spectroscopy*, vol. 50, No. 2, 1996, pp. 263-269.

Schaeberle, et al., "Raman Chemical Imaging: Histopathology of Inclusions in Human Breast Tissue,"*Analytical Chemistry*, vol. 68, No. Jun. 1, 1996, pp. 1829-1833.

Kidder, et al., "Mercury cadmium telluride focal-plane array detection for mid-infrared Fourier-transform spectroscopic imaging,"*Optics Letters*, vol. 22, No. 10, May 15, 1997, pp. 742-744.

Lewis, et al., "Si: As Focal-Plane Array Detection for Fourier Transform Spectroscopic Imaging in the Infrared Fingerprint Region,"*Applied Spectroscopy*, vol. 51, No. 4, 1997, pp. 563-567.

Strane, et al., "Assessment of Tissue Viability Using Near-Infrared Spectroscopy,"*British Journal of Plastic Surgery*, 1998, pp. 210-217.

Mansfield, et al., "Fuzzy C-Means Clustering and Principal Component Analysis of Time Series from Near-Infrared Imaging of Forearm Ischemia,"*Computerized Medical Imaging and Graphics*, vol. 21, No. 5, Sep.-Oct. 1997, pp. 299-308.

Mansifled, et al., "Analysis of Spectroscopic Imaging Data by Fuzzy C-Means Clustering,"*Analytical Chemistry*, vol. 69, No. 16, Aug. 15, 1997, pp. 3370-3374.

Sowa, et al., "Noninvasive Assessment of Regional and Temporal Variations in Tissue Oxygenation by Near-Infrared Spectroscopy and Imaging,"*Applied Spectroscopy*, vol. 51, No. 2, 1997, pp. 143-152.

Waynant, et al., Overview of Non-Invasive Fluid Glucose Measurement Using Optical Techniques to Maintain Glucose Control in Diabetes Mellitus, *LEOS Newsletter*, Apr. 1998, pp. 3-38.

Klonoff, "Noninvasive Blood Glucose Monitoring,"*Diabetes Care*, vol. 20, No. 3, Mar. 1997, pp. 433-437.

Qu, et al., "Monte Carlo Modeling Studies of the Effect of Physiological Factors and Other Analysis on the Determination of Glucose Concentration In Vivo by Near Infrared Optical Absorption and Scattering Measurements,"*Journal of Biomedical Optics*, vol. 2, No. 3, Jul. 1997, pp. 319-325.

Bruulsema, et al., "Correlation Between Blood Glucose Concentration in Diabetics and Noninvasively Measured Tissue Optical Scattering Coefficient,"*Optical Letters*, vol. 22, No. 3, Feb. 1997, pp. 190-192.

Kohl, et al., "Influence of Glucose Concentration on Light Scattering in Tissue-Simulating Phantoms,"*Optics Letters*, vol. 19, No. 24, Dec. 1994, pp. 2170-2172.

Maier, et al., "Possible Correlation Between Blood Glucose concentration and the Reduced Scattering Coefficient of Tissues in the Near Infrared,"*Optics Letters*, vol. 19, No. 24, Dec. 1994, pp. 2062-2064.

Kidder, et al., "Visualization of silicone gel in human breast tissue using new infrared imaging spectroscopy,"*Nature Medicine*, vol. 3, No. 2, Feb. 1997, pp. 235-237.

Afromowitz, et al., "Multispectral Imaging of Burn Wounds: A New Clinical Instrument for Evaluating Burn Depth, "*IEEE Transactions on Biomedical Engineering*, vol. 35, No. 10, Oct. 1988, pp. 842-850.

McKeena, et al., "Integration of Visible/NIR Spectroscopy and Multispectral Imaging for Poultry Carcass Inspection, "*Journal of Food Engineering*, vol. 30, 1996, pp. 195-207.

Hardin, R. Winn, "Hyperspectral Imaging: How Much is Hype?"*Photonics Spectra*, Jul. 1997, pp. 82-92.

* cited by examiner

MULTISPECTRAL/HYPERSPECTRAL MEDICAL INSTRUMENT

This application claims the benefit of provisional application No. 60/093,041, filed Nov. 10, 1997.

FIELD OF THE INVENTION

The invention relates to a surgical and diagnostic instrument for performing real-time general-purpose imaging during surgery, clinical procedures, or other medical evaluations.

BACKGROUND OF THE INVENTION

Spectroscopic imaging devices which employ Acousto-Optic Tunable Filters (AOTF), Liquid Crystal Tunable Filters (LCTF), or dispersive gratings are known. Such devices have been used for microscopy and remote sensing.

SUMMARY OF THE INVENTION

Generally, the invention features a medical instrument that includes an optic responsive to a surface of tissue of a patient, a spectral separator optically responsive to the optic, and an imaging sensor optically responsive to the spectral separator. The instrument also includes a diagnostic processor having an image acquisition interface responsive to the imaging sensor and a filter control interface to which the spectral separator is responsive.

The spectral separator can be a tunable filter, such as a liquid crystal tunable filter, and the imaging sensor can be a two-dimensional imaging array, such as a charge coupled device. The optic can include a macro lens, an adjustable lens, or a probe that includes an imaging fiber optic cable, and a stand can be connected relative to the optic to position the optic relative to the patient. The control interface can be operable to adjust the filter at least twenty times to acquire hyperspectral data for redisplay in real time. The medical instrument can perform diagnostic processing for images acquired exclusively under visible light.

The diagnostic processor can also include a general-purpose processing module and diagnostic protocol modules, which can each include filter transfer functions and an image processing protocol. The general-purpose processing module can be operative to instruct the filter to successively apply the filter transfer functions to light collected from the patient, to acquire from the imaging sensor a number of images of the collected light each obtained after one of the filter transfer functions is applied, and to process the acquired images according to the image processing protocol to obtain a processed display image. The general-purpose processor can be a real-time processor operative to generate a processed display image within a time period on the order of the persistence of human vision. It may also be operative to acquire some images more slowly depending on the number of wavelengths and complexity of diagnostic processing protocol. The sensor and filter can be operative in the visible, infra-red, and UV regions.

Instruments according to the invention are advantageous in that they can permit a surgeon or a physician to diagnose a medical condition or develop a surgical strategy based on real-time images obtained during surgery or in the course of performing clinical procedures or other medical evaluations. The physician may therefore be able to obtain significantly more information about a patient's condition than he might otherwise have been able to assemble by presenting an interactive interface. This additional information may permit a given surgical procedure to be carried out more precisely and may lead to more successful surgical results. It may also enhance the precision and results of other types of medical evaluations and procedures.

The general-purpose nature of the instrument can also help the surgeon develop significant amounts of medical information in time-critical surgical situations. For example, a patient may undergo relatively straight-forward surgery during which the surgeon may discover a tumor or another internal condition. With an instrument according to the invention, the physician can spend a small amount of additional time with the patient under anesthesia and determine the nature and extent of the tumor. This can be particularly beneficial during major surgery, where extending surgery duration poses a potential morbidity and mortality risk. Because the procedure is rapid and noninvasive, the patient is exposed to little additional risk. The benefit of immediate diagnosis and evaluation is significant.

An instrument according to the invention may also be able to provide a wide variety of diagnostic capabilities, allowing a physician to enhance the capabilities of his or her practice substantially in a variety of different realms, without investing in a number of instruments. The physician can then enhance or update the instrument by the adding software modules that are specifically targeted towards certain conditions of particular tissues, subsystems, or disease states. This can allow a single base instrument to be configured for a variety of different types of practices, and priced according to the type of practice to be served by the instrument. For example, a general-purpose instrument to be used by a general surgeon could include a package of diagnostic protocols that would permit the diagnosis of a variety of conditions that a general surgeon might encounter, while a neurosurgeon's module might be added to allow a specialist to detect particular conditions within the brain. Electronic and optical upgrades may also be provided to update, specialize, or improve the performance of the instrument. Such upgrades can include processing modules, memory boards, lenses, and the like.

DETAILED DESCRIPTION OF AN ILLUSTRATIVE EMBODIMENT

Figure 1:
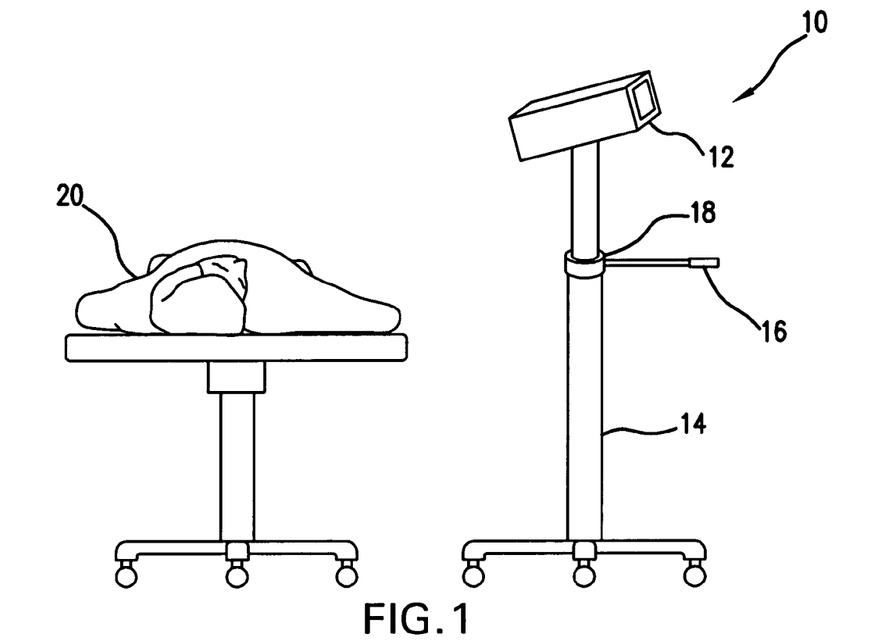
FIG. 1 is a perspective diagram of a macroscopic instrument according to the invention.

Referring to FIG. 1, an instrument according to the invention 10 includes an imaging module 12 mounted on a surgical stand 14. In this embodiment, the surgeon can direct the imaging portion 12 towards a patient 20 by manipulating a control 16 that adjusts the attitude of the imaging portion through a positioning mechanism 18.

Figure 2:
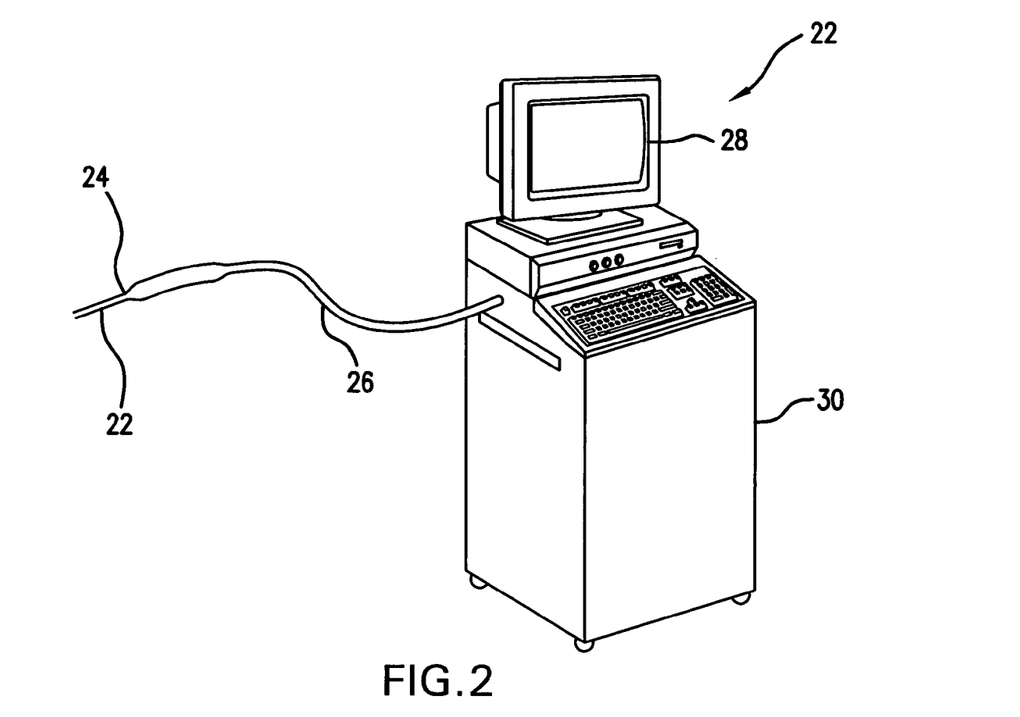
FIG. 2 is a perspective diagram of a rigid or flexible probe-based instrument according to the invention.

Referring to FIG. 2, an alternative embodiment of the invention 22 may include a probe such as a rigid or flexible endoscopic, thoracoscopic, laproscopic, or angioscopic probe 24 connected to an imaging station 30 via a fiber-optic cable 26. The surgeon can manipulate the probe within the patient in a minimally-invasive surgical procedure and derive images from a portion of the patient and display these images on a display 28. A medical implement 32, such as a laser, can also be provided through the probe. For example, after diagnosing a particular condition, a physician can begin laser ablation therapy to remedy it.

Figure 3:
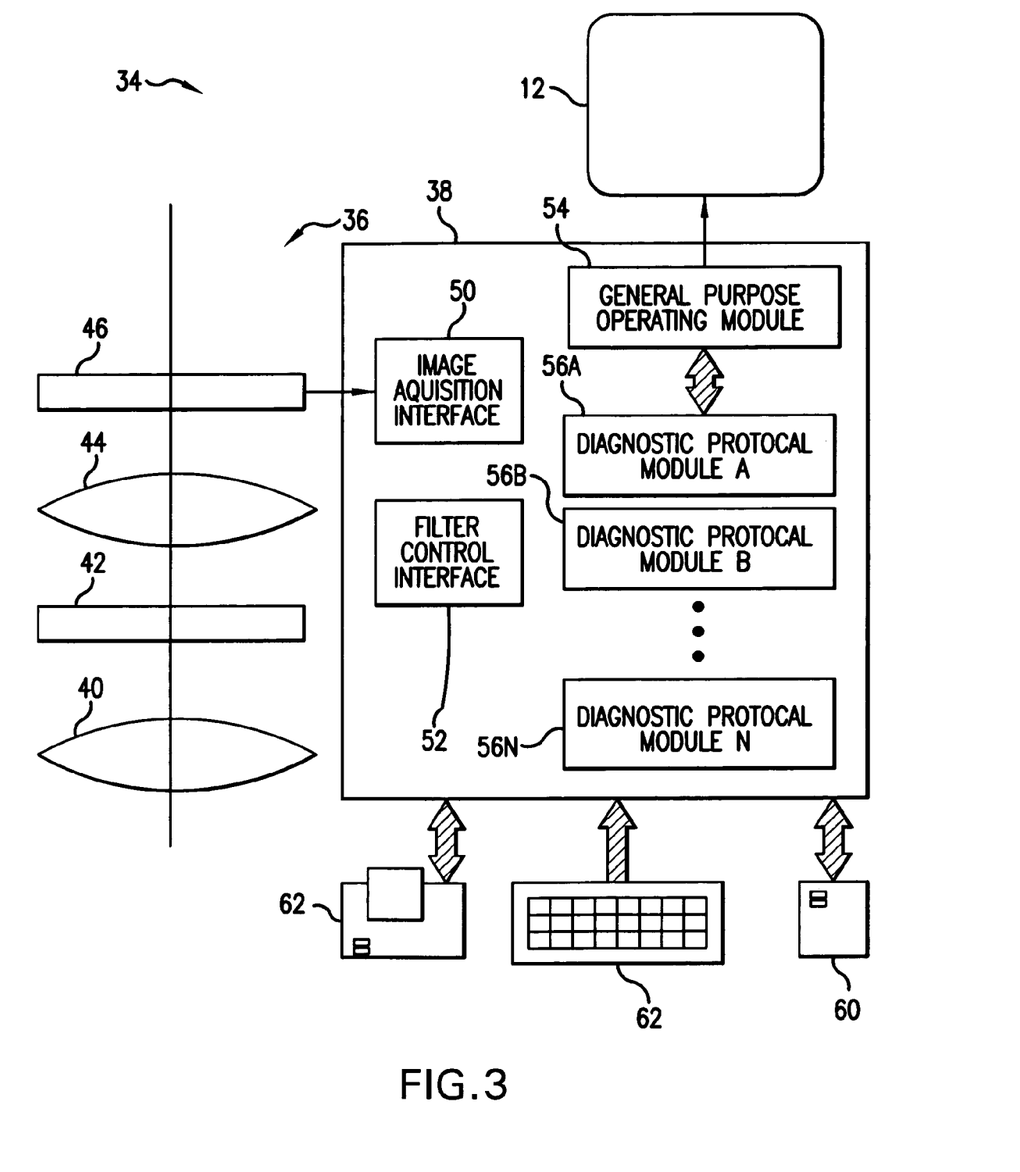
FIG. 3 is a block diagram of the instrument of FIG. 1.

Referring to FIG. 3, a medical instrument according to the invention 34 may include an optical acquisition system 36 and a diagnostic processor 38. The acquisition system 36 includes a first-stage imaging optic 40, a Liquid Crystal Tunable Filter (LCTF) 42, a second-stage optic 44, and an imaging element 46. The first-stage optic receives light collected from the patient and focuses it onto the surface of the LCTF. The first-stage optic can be a simple or compound macro lens in the case of a macroscopic instrument (FIG. 1). In a probe-based instrument (FIG. 2), the first stage optic can include imaging optics within a probe such as a endoscopic, laproscopic, thoracoscopic, or angioscopic probe. The first stage lens can also be adjustable, allowing a physician to scan larger areas of tissue and then zoom into particular regions.

The LCTF 42 is a programmable filter that filters out all but a wavelength region of interest from the light collected from the patient. The second-stage optic 44 receives the remaining light from the LCTF and focuses it onto the image sensor 46. The image sensor is preferably, although not necessarily, a two-dimensional array sensor, such as a charge-coupled device array (CCD), which delivers an image signal to the diagnostic processor 38.

The diagnostic processor 38 includes an image acquisition interface 50, that has an input responsive to an output of the image sensor 46 and an output provided to a general-purpose operating module 54. The general-purpose operating module includes routines that perform image processing, and that operate and control the various parts of the system. It has a control output provided to a filter control interface 52, which in turn has an output provided to the LCTF 42. The general-purpose operating module also interacts with a number of diagnostic protocol modules 56A, 56B, . . . 54N, and has an output provided to the video display 12. The diagnostic processor can include special purpose hardware, general-purpose hardware with special-purpose software, or a combination of the two. The diagnostic processor also includes an input device 58, which is operatively connected to the general-purpose operating module. A storage device 60, and a printer are also operatively connected to the general-purpose operating module.

Figure 4:
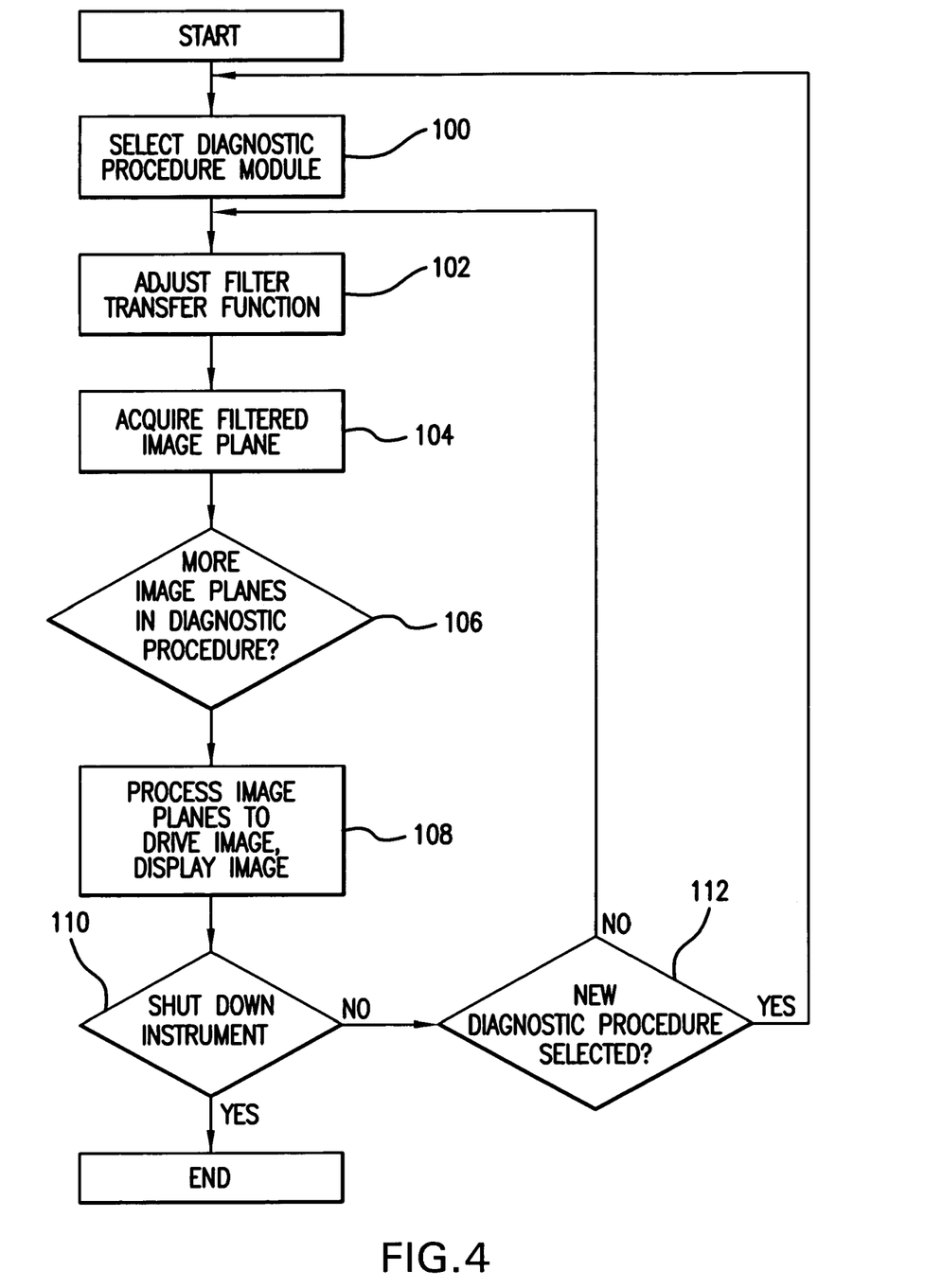
FIG. 4 is a flowchart illustrating the operation of the system of FIG. 1.

In operation, referring to FIGS. 3 and 4, a surgeon employing the instrument begins by selecting a diagnostic protocol module using the instrument's input device (step 100). Each diagnostic protocol module is adapted to detect particular characteristics of the surface of one or more types of tissue. For example, the surgeon might select a module which enhances the visibility of cancerous tissue. The surgeon would then direct the camera at the area of interest and begin inspecting it either under ambient light or with the aid of a supplemental light source, which can be filtered to emphasize particular special characteristics of the light it emits.

The diagnostic processor 38 responds to the surgeon's input by obtaining a series of filter transfer functions and an image processing protocol from the selected diagnostic protocol module 56. The diagnostic processor provides the filtering transfer functions to the LCTF 42 via its filter control interface 52 (step 102) and then instructs the image acquisition interface 50 to acquire and store the resulting filtered image from the image sensor 46 (step 104). The general-purpose operating module 54 repeats these filtering and acquiring steps one or more times, depending on the number of filter transfer functions stored in the selected diagnostic protocol module (see step 106). The filtering transfer functions can represent bandpass, multiple bandpass, or other filter characteristics.

Once the image acquisition interface 50 has stored images for all of the image planes specified by the diagnostic protocol chosen by the surgeon, it begins processing these image planes based on the image processing protocol from the selected diagnostic protocol module 56N (step 108). Processing operations can include general image processing of combined images, such as comparing the relative amplitude of the collected light at different wavelengths, adding amplitudes of the collected light at different wavelengths, or computing other combinations of signals corresponding to the acquired planes. The processing operations can also include more complex multivariate statistical techniques to compute the image (e.g., chemometrics). The computed image is displayed on the display 12. It can also be stored in the storage device 60 or printed out on the printer 62.

The processing operations can also be based on a diagnostic knowledge base. This database can include data resulting from the comparison between optical and actual diagnoses. Each instrument can also continuously update its database as it is used to perform diagnoses, thereby steadily expanding its diagnostic capabilities.

In order to provide a real-time or near-real-time image to the surgeon, the instrument repeatedly acquires planes and processes them to develop an image to be displayed to the surgeon. This allows the surgeon to move the instrument, or to view moving organs, such as a beating heart. This constant acquisition and processing continues until the surgeon either turns the instrument off (step 110) or selects a different imaging mode (step 112). The diagnostic processor 38 preferably has sufficient processing power to update the screen in this way at video rates (i.e., about 30 frames per second), although rates as low as a few frames per second may work quite well, and rates as low as one frame per minute may be adequate for many purposes. On slower instruments, general lock-in schemes or other tracking modalities, such as cardiac gating, can be used to remove motion artifacts due to breathing or heart beat. Frame rate may also be variable, depending on the number of wavelengths and the complexity of the diagnostic procedure.

Preferably, the instrument can operate in multispectral, and hyperspectral, or even ultraspectral imaging modes. Multispectral modes involve image processing derived from a relatively small number of spectral image planes (two wavelengths to about twenty wavelengths). Hyperspectral and ultra spectral imaging modes involve at least twenty image planes and can produce significantly more accurate and informative results. Ultraspectral modes involve hundreds of wavelengths, and may be able to produce even further information about the patient. Hyperspectral and ultraspectral imaging may include selecting specific wavelength bands for discrimination of a particular diseased states, or it may also allow the instrument to scan for multiple conditions at the same time.

It is also contemplated that both types of instrument can operate in connection with an excitation source, such as an ultraviolet lamp and IR source, or other means of spectral illumination or a laser to enhance the received images. Although such excitation may not be necessary, it may allow for the examination of different optical phenomenon and provide additional diagnostic information. And both emission and reflectance modes can be combined in a diagnostic procedure either simultaneously or sequentially. Relative utilization of different emission or reflection measurements involved in the same diagnostic procedure can be obtained by modulating the different sources. The instrument can also develop light from bioluminescent sources introduced into the patient.

Instruments according to the invention can also operate to process images from image planes acquired at wavelengths outside of the visible region. In one particular embodiment, the instrument is sensitive to the visible and near infra-red regions. It is also contemplated that far infra-red be included to allow the instrument to sense molecular-specific rotational modes.

An example of operation would include the use of a diagnostic protocol module that examined a first wavelength of about 550 and a second wavelength of about 575 associated with oxy- and deoxy-hemoglobin to determine blood oxygenation. The relationship between these wavelengths is described in "Hemoglobin: Molecular Genetics and Clinical Aspects," by H. Franklin Bunn and Bernard Forget, W. B. Sanders, 1986. Another example would include the use of a diagnostic protocol module for examining the Fourier transform infra-red spectra of the colon and rectum as described in "Human Colorectal Cancers Display Abnormal Fourier Transform Spectra, " by Basil Rigas et al., Proceedings of the National Academy of Science, pp. 8140–8144, 1987.

Surgical and medical applications of instruments according to the invention can include, but are not limited to, determining tissue viability (i.e. whether tissue is dead or living tissue and whether it is predicted to remain living), detecting tissue ischemia (e.g., in heart, or in leg after a gunshot wound, differentiating between normal and malignant cells and tissues (e.g., delineating tumors, dysplasias and precaucerous tissue, detecting metastasis), differentiating between of infected and normal (but inflamed) tissue (e.g., extent of aortic root infection), quantification and identification of pathogens, (e.g., bacterial count of burn wounds and differentiating and delineating other pathologic states. Application can also include tissue, blood chemistry, and blood flow (including oxy- and deoxyhemoglobin, myoglobin deoxymyoglobin, cytochrome, pH, glucose, calcium and other elements or biological compounds alone or in combination). The instrument can also be applied by veterinarians to animals and by dentists to dental applications, such as peridental disease.

The present invention has now been described in connection with a number of specific embodiments thereof. However, numerous modifications which are contemplated as falling within the scope of the present invention should now be apparent to those skilled in the art. Therefore, it is intended that the scope of the present invention be limited only by the scope of the claims appended hereto. In addition, the order of presentation of the claims should not be construed to limit the scope of any particular term in the claims.

What is claimed is:

1. A medical instrument comprising:
    a first-stage optic responsive to illumination of a viable tissue of a patient;
    a spectral separator optically responsive to the first stage optic and having a control input;
    an imaging sensor optically responsive to the spectral separator and having an image data output; and
    a diagnostic processor having an image acquisition interface with an input responsive to the imaging sensor;
    a filter control interface having a control output provided to the control input of the spectral separator, which directs the spectral separator independently of the illumination to receive wavelengths of the illumination that provide multispectral or hyperspectral information as determined by a set of instructions from a diagnostic protocol module; and
    a general-purpose operating module, and a plurality of diagnostic protocol modules;
    wherein each diagnostic protocol module is organ or tissue specific and contains the set of instructions for operating the spectral separator via the filter control interface and for operating the image acquisition interface.

2. The medical instrument of claim 1, wherein the spectral separator is a filter.

3. The medical instrument of claim 1, wherein the imaging sensor is a two-dimensional imaging array.

4. The medical instrument of claim 1, wherein the imaging sensor includes a charge coupled device.

5. The medical instrument of claim 1, wherein the imaging sensor includes an infra-red sensitive focal plane array.

6. The medical instrument of claim 1, includes memory for storing the image data acquired from the image sensor.

7. The medical instrument of claim 1, wherein the first-stage optic is a macro lens.

8. The medical instrument of claim 1, wherein the first stage optic is an adjustable lens.

9. The medical instrument of claim 1, further including a stand connected relative to the first-stage optic to position the first-stage optic relative to the patient.

10. The medical instrument of claim 1, further comprising:
    a probe; and
    an imaging fiber optic cable.

11. The medical instrument of claim 10, further including a surgical implement attached to the probe.

12. The diagnostic processor of claim 10, wherein the optical acquisition system comprises a lens optically responsive to a viable tissue of a patient.

13. The diagnostic processor of claim 10, wherein the optical acquisition system comprises a probe.

14. The medical instrument of claim 1, wherein the filter control interface is operable to adjust the spectral separator at least two times to acquire multispectral data for redisplay in real time.

15. The medical instrument of claim 1, wherein the set of instructions in each of the diagnostic protocol modules includes an image processing protocol, wherein the general-purpose operating module is operative to instruct the spectral separator to successively collect a plurality of images from the patient, wherein the general-purpose operating module is operative to acquire from the imaging sensor the plurality of images, and wherein the general-purpose operating module is operative to process the acquired plurality of images according to the diagnostic processing protocol to obtain a processed display image.

16. The medical instrument of claim 15, wherein the general-purpose operating module is a real-time processor operative to generate a processed display image within a time period on the order of the persistence of human vision.

17. The medical instrument of claim 15, wherein the general-purpose operating module is a processor operative to generate a processed display image within about five minutes.

18. The medical instrument of claim 15, wherein the general-purpose operating module is operative to acquire images within different time constraints depending on a number of wavelengths, and a complexity and a sensitivity of the diagnostic protocols.

19. The medical instrument of claim 1, wherein the set of instructions in each of the diagnostic protocol modules includes a predetermined image processing protocol adapted to detect particular characteristics of one or more types of tissue, organ disease or trauma, wherein the general-purpose operating module is operative to instruct the spectral separator to collect a plurality of images from the patient, wherein the general-purpose operating module is operative to acquire from the imaging sensor the plurality of images collected, and wherein the general-purpose operating module is operative to process the acquired images according to the diagnostic processing protocol to obtain a processed display image.

20. The medical instrument of claim 1, wherein the diagnostic processor includes a real-time processor operative to generate a processed display image within a time period on the order of the persistence of human vision.

21. The medical instrument of claim 1, wherein the diagnostic processor is operable to perform diagnostic processing for images acquired from a source that includes visible light.

22. The medical instrument of claim 1, wherein the filter and sensor are operable in the visible and far infra-red regions.

23. The medical instrument of claim 1, wherein the filter and sensor are operable in the ultra-violet, visible, and infra-red regions.

24. The medical instrument of claim 1, wherein the diagnostic processor performs spectral data processing.

25. The medical instrument of claim 1, wherein the diagnostic processor is modular and upgradeable by adding additional diagnostic protocol modules, thereby expanding diagnostic capabilities.

26. The medical instrument of claim 1, further comprising a supplemental light source.

27. The medical instrument of claim 26, wherein both light emission and reflectance modes are combined in a diagnostic procedure either simultaneously or sequentially.

28. The diagnostic processor of claim 1, wherein the imaging sensor is a charged-coupled device.

29. The diagnostic processor of claim 1, further comprising an optical acquisition system.

30. The diagnostic processor of claim 1, wherein the imaging processor provides processed images to the image output device within a time period on the order of the persistence of human vision.

31. A method for acquiring an image, comprising the steps of:
  receiving light at a first-stage optic collected from a viable tissue of a patient;
  transmitting the light using the first-stage optic through a spectral separator, wherein the spectral separator has a control input;
  removing all of the light except for a wavelength region of interest in the spectral separator, wherein the remaining light is spectrally resolved light;
  transmitting the spectrally resolved light to an imaging sensor, wherein the imaging sensor has an image data output;
  generating an image signal;
  outputting the image signal to a diagnostic processor; and
  acquiring the image signal at the diagnostic processor, wherein the diagnostic processor has an image acquisition interface with an input responsive to the imaging sensor, a filter control interface having a control output provided to the control input of the spectral separator, which directs the spectral separator independently of the illumination to receive multiple selected wavelengths of the illumination that provides multispectral or hyperspectral information as determined by a set of instructions from one or more diagnostic protocol modules, a general-purpose operating module, wherein each diagnostic protocol module is organ specific disease specific, trauma specific or tissue specific and contains a set of instructions for operating the spectral separator via the filter control interface and for operating the image acquisition interface.

32. The method of claim 31, wherein the spectral separator is a filter.

33. The method of claim 31, wherein the imaging sensor is a two-dimensional imaging array.

34. The method of claim 31, wherein the imaging sensor includes an infra-red sensitive focal plane array.

35. The method of claim 31, further comprising the steps of storing the image data acquired from the image sensor.

36. The method of claim 31, wherein the first-stage optic is a macro lens.

37. The method of claim 31, wherein the first-stage optic is an adjustable lens.

38. The method of claim 31, wherein the first-stage optic is disposed in a probe that includes an imaging fiber optic cable.

39. The method of claim 38, wherein the probe is a surgical instrument.

40. The method of claim 31, further comprising the step of operating the control interface to adjust the filter at least two times to acquire multispectral data for redisplay in real-time.

41. The method of claim 31, further comprising the steps of:
  instructing the spectral separator to successively collect a plurality of images from the patient, wherein the set of instructions in each of the diagnostic protocol modules includes an image processing protocol;
  acquiring from the imaging sensor the plurality of images of the collected light; and
  processing the acquired images according to the diagnostic processing protocol to obtain a processed display image.

42. The method of claim 41, further comprising the step of generating a processed display image within a time period on the order of the persistence of human vision.

43. The method of claim 41, wherein the general-purpose operating module is a processor operative to generate a processed display image within about five minutes.

44. The method of claim 41, wherein the general-purpose operating module is operative to acquire some images within different time constraints depending on a number of wavelengths, and a complexity and a sensitivity of the diagnostic protocols.

45. The method of claim 31, further comprising the steps of:
  instructing the spectral separator to successively collect a plurality of images from the patient, wherein the set of instructions in each of the diagnostic protocol modules includes a predetermined image processing protocol adapted to detect particular characteristics of the one or more types of tissues;
  acquiring from the imaging sensor the plurality of images of the collected light; and
  processing the acquired images according to the diagnostic processing protocol to obtain a processed display image.

46. The method of claim 31, wherein the diagnostic processor includes a real-time processor operative to generate a processed display image within a time period on the order of the persistence of human vision.

47. The method of claim 31, wherein the diagnostic processor is operable to perform diagnostic processing for images acquired from a source that includes visible light.

48. The method of claim 31, wherein the filter and sensor are operable in the visible and far infra-red regions.

49. The method of claim 31, wherein the filter and sensor are operable in the ultra-violet, visible, and infra-red regions.

50. The method of claim 31, further comprising the step of:
selecting a diagnostic protocol module from a plurality of diagnostic protocol modules, wherein the selected diagnostic protocol is adapted to detect particular characteristics of one or more types of tissue.

51. The method of claim 50, further comprising the step of directing the first-stage optic to a tissue area of interest.

52. The method of claim 31, wherein the diagnostic processor is operable to perform diagnostic processing for images acquired from a supplemental light source which may filtered to emphasize particular special characteristics of the light it emits.

53. The method of claim 31, wherein the diagnostic processor performs statistical techniques to compute an image.

54. The method of claim 31, wherein the diagnostic processor is modular and upgradeable by adding additional diagnostic protocol modules, thereby expanding diagnostic capabilities.

55. The method of claim 31, further comprising the step of generating light from a supplemental light source.

56. The method of claim 31, wherein both light emission and reflectance modes are combined in a diagnostic procedure either simultaneously or sequentially.

57. The method of claim 31, wherein the diagnostic protocol performs tissue oxygenation mapping.

58. The method of claim 31, wherein the diagnostic protocol performs tissue viability mapping.

59. The method of claim 31, wherein the diagnostic protocol performs a diagnosis of normal versus abnormal tissue.

60. The method of claim 31, wherein the diagnostic protocol performs tissue ischemia detection.

61. The method of claim 31, wherein the diagnostic protocol performs cancer detection or diagnosis.

62. A multi-spectral diagnostic imaging method comprising the steps of:
collecting broad-band light from a viable tissue surface of a patient;
acquiring a number of images, wherein said number is equal to or greater than two; and
each image is acquired by an acquisition method comprising the step of:
applying a filter to filter out all but a particular region of interest from the light collected from said patient surface;
specifying said region of interest according to a diagnostic protocol, wherein said diagnostic protocol is adapted to detect characteristics of said patient surface area, independently of the wavelength of illumination to provide multispectral or hyperspectral information as determined by a set of instructions from the diagnostic protocol module; and
processing said number images to obtain a display image.

63. The method of claim 62, wherein said light is selected from the group consisting of: infra-red, ultraviolet, visible, and any combination thereof.

64. The method of claim 62, wherein said particular wavelength region of interests are not identical.

65. The method of claim 62, wherein said number is equal to or greater than twenty.

66. The method of claim 62, wherein said number is equal to or greater than one hundred.

67. The method of claim 62, further comprising the step of adjusting said area to collect light from larger or smaller patient tissue surface areas.

68. The method of claim 62, wherein said processing step comprises, alternatively, the step of:
combining said number of images;
comparing relative amplitudes of the collected light at different wavelengths;
adding amplitudes of the collected light at different wavelengths; or
performing statistical techniques.

69. The method of claim 68, further comprising the step of:
displaying said display image;
storing said display image; or
printing said display image.

70. The method of claim 62, wherein said processing step is based on a diagnostic knowledge base.

71. The method of claim 62, further comprising the step of
exciting said patient surface area with an excitation source, wherein said excitation source is an ultraviolet lamp, IR source, laser, or other means of spectral illumination.

72. The method of claim 62, wherein said characteristics are selected from the group consisting of: tissue viability, tissue ischemia, malignancy, infection, pathology, blood chemistry, blood flow, or any combination thereof.

73. A diagnostic processor configured to control acquisition, processing and display of images, comprising:
a source for illuminating a viable tissue;
a plurality of diagnostic protocol modules comprising instructions for the acquisition and processing of images that provide hyperspectral or multispectral information, wherein the diagnostic protocol modules are tissue specific, organ specific, disease specific or trauma specific;
a user input for allowing a user to select a diagnostic protocol module from the plurality of diagnostic protocol modules;
a spectral separator configured to filter broad-band light reflected or emitted from the viable tissue, wherein the spectral separator is controlled by instructions from the selected diagnostic protocol module, and further wherein the spectral separator is operated independently of a wavelength of the source;
an imaging sensor configured to collect light filtered by the spectral separator, wherein the imaging sensor is controlled by instructions from the selected diagnostic protocol module;
an image processor configured to process images collected by the imaging sensor, wherein the image processor is controlled by instructions from the selected diagnostic protocol module; and
an image output device for providing output of the hyperspectral or mulspectral information from the image processor.

74. The diagnostic processor of claim 73, wherein one or more of the diagnostic protocol modules comprises instructions that the image processor process multispectral images.

75. The diagnostic processor of claim 73, wherein one or more of the diagnostic protocol modules comprises instructions that the image processor process hyperspectral images.

76. The diagnostic processor of claim 73, wherein one or more of the diagnostic protocol modules comprises instructions that the image processor process ultraspectral images.

77. The diagnostic processor of claim 73, wherein one or more of the diagnostic protocol modules comprises instructions for the display of images.

78. The diagnostic processor of claim 73, wherein the image output device is controllable by instructions from a diagnostic protocol module.

79. The diagnostic processor of claim 73, wherein one or more of the diagnostic protocol modules is modifiable by user input.

80. The diagnostic processor of claim 73, wherein the diagnostic protocol modules may be added or removed by a user.

81. A method of imaging a tissue comprising:
illuminating a tissue;
selecting a diagnostic protocol module from a diagnostic processor, wherein the diagnostic processor comprises a plurality of tissue-specific, organ-specific, disease specific or trauma specific diagnostic protocol modules, further wherein the diagnostic protocol modules comprise instructions for the acquisition and processing of images;
filtering broad-band light reflected and/or emitted from the tissue using a spectral separator controlled by instructions from the selected diagnostic protocol module, wherein the spectral separator is operated independent of the illumination wavelength;
collecting the light passed by the spectral separator with an imaging sensor, wherein the imaging sensor is controlled by the selected diagnostic protocol module;
processing images collected by the imaging sensor with an image processor, wherein the image processor is controlled by instructions from the selected diagnostic protocol module; and
displaying one or more processed images.

82. The method of claim 81, wherein the step of illuminating the viable tissue comprises illumination with an unfiltered light.

83. The method of claim 81, wherein the step of illuminating the viable tissue comprises illumination with filtered light.

84. The method of claim 81, wherein the filtering of the spectral separator is independent of the illumination wavelength.

85. The method of claim 81, wherein the step of processing images comprises multispectrally processing images.

86. The method of claim 81, wherein the step of processing images comprises hyperspectrally processing images.

87. The method of claim 81, wherein the step of processing images comprises ultraspectrally processing images.

* * * * *

UNITED STATES PATENT AND TRADEMARK OFFICE
CERTIFICATE OF CORRECTION

| | |
|---|---|
| PATENT NO. | : 6,937,885 B1 |
| APPLICATION NO. | : 09/182898 |
| DATED | : August 30, 2005 |
| INVENTOR(S) | : Edgar N. Lewis and Jenny E. Freeman |

It is certified that error appears in the above-identified patent and that said Letters Patent is hereby corrected as shown below:

On the Title page, item [60] "Related U.S. Application Data":
"Application No. 08/961,294, filed on October 30, 1997" should be added.

On the Title page, item [75] "Inventors":
"Dr. E. Neil Lewis, Brookeville, MD (US)" should be deleted.

Signed and Sealed this

First Day of May, 2007

JON W. DUDAS
*Director of the United States Patent and Trademark Office*